United States Patent [19]

Tsuji et al.

[11] Patent Number: 4,483,924
[45] Date of Patent: Nov. 20, 1984

[54] SYSTEM FOR CONTROLLING A PRINTER IN A BLOOD SUGAR ANALYZER

[75] Inventors: Nobuhiko Tsuji; Keijiroh Nakamura, both of Yokosuka; Koichi Endoh, Hino; Toshiyoshi Hamada; Keiichi Ishida, both of Tokyo, all of Japan

[73] Assignee: Fuji Electric Company, Ltd., Kanagawa, Japan

[21] Appl. No.: 324,147

[22] Filed: Nov. 23, 1981

[30] Foreign Application Priority Data

Dec. 9, 1980 [JP] Japan ................. 55-172660
Dec. 9, 1980 [JP] Japan ................. 55-172657

[51] Int. Cl.³ .................. G01N 35/00; G01N 33/66
[52] U.S. Cl. ........................... 435/288; 204/195 B; 204/1 T; 204/403; 364/415; 364/416; 364/497; 435/291; 435/817; 436/50
[58] Field of Search .................. 422/81; 435/288; 204/195 B, 1 T; 364/415, 416, 497

[56] References Cited

U.S. PATENT DOCUMENTS

| | | | |
|---|---|---|---|
| 3,542,662 | 11/1970 | Hicks | 435/190 X |
| 3,770,607 | 11/1973 | Williams | 204/195 B X |
| 3,902,970 | 9/1975 | Levin | 204/195 B X |
| 3,920,969 | 11/1975 | Berglas | 204/195 B X |
| 4,224,405 | 9/1980 | Hijikata | 435/288 X |

*Primary Examiner*—Sidney Marantz
*Attorney, Agent, or Firm*—Brumbaugh, Graves, Donohue & Raymond

[57] ABSTRACT

A blood sugar analyzer has a reaction cell which houses a fixed enzyme membrane and measuring electrode and which receives a blood specimen, to cause a chemical reaction between the specimen and membrane for measuring the blood sugar concentration in the specimen on the basis of the reaction current generated in the electrode by the reaction. The analyzer also monitors the temperature in the cell and the sensitivity of the electrode, and a printer prints out data on the temperature and sensitivity. A digital control device controls overall operation of the analyzer.

4 Claims, 7 Drawing Figures

SYSTEM FOR CONTROLLING A PRINTER IN A BLOOD SUGAR ANALYZER

BACKGROUND OF THE INVENTION

TECHNICAL FIELD

The present invention relates to a total-bloodtype blood sugar analyzer for use in hospitals, clinics, and analyzer companies for analyzing the concentration of glucose or blood sugar in a blood specimen (total blood, blood serum, or blood plasma of a human being or animal) in a short period of time using a small amount of blood sample, and more particularly to blood sugar analyzer having means for monitoring the operation of the analyzer and means for printing out results of monitoring and analysis.

When a microcomputer is used for overall control of a blood sugar analyzer, the overall apparatus can be quite complicated, can require an increased expenditure of labor for maintenance and troubleshooting at least in part because the operator or technician may be required to study a complex circuit contained in the analyzer. The typical enzyme membrane sensor in the analyzer operates on an electrochemical reaction, and hence is susceptible to ambient temperatures and tends to become deteriorated quickly. Therefore, maintenance of the analyzer is needed to monitor and control ambient temperatures, and to monitor the degree of sensor deterioration.

It has been a customary practice for maintenance personnel to check various points of the circuit with an oscilloscope, a tester and/or other instruments when monitoring or servicing the analyzer. However, with a large number of points to be monitored, the expenses due to time and labor for the maintenance are considerably increased. Accordingly, it would be beneficial to provide an analyzer with means for easily monitoring the operation of the analyzer, and for indicating the results of monitoring to the operator.

SUMMARY OF THE INVENTION

It is accordingly an object of the present invention to record data on conditions of various parts in a blood sugar analyzer on an associated printer to allow an operator to make decisions based on the recorded data, thus reducing time, labor and expenses necessary for maintenance of the overall analyzer.

Another object of the present invention is to incorporate a printer interface function in a digital control device such as a microcomputer, thus providing an interface control system by which an interface device used exclusively with a printer is simplified in construction and function, for inexpensive and simple communication with the printer on a real-time basis.

The present invention resides in having parts of an analyzer, particulary a sensor, monitored by a printer, and where the printer itself can be checked for its normal operation by causing the printer to print a predetermined character pattern.

The present invention is also characterized in that a synchronous signal from a printer is assigned as an interrupting signal (restart command signal), for a microcomputer to transfer to a mode of operation under a printer control operation for controlling printing operation of the printer. Stated otherwise, an interface device is simplified by incorporating a printer interface function in a control device.

Numerous other advantages and features of the present invention will become readily apparent from the following detailed description of the invention and of one embodiment thereof, from the claims and from the accompanying drawings.

DETAILED DESCRIPTION OF THE PREFERRED EMBODIMENT

Figure 1:
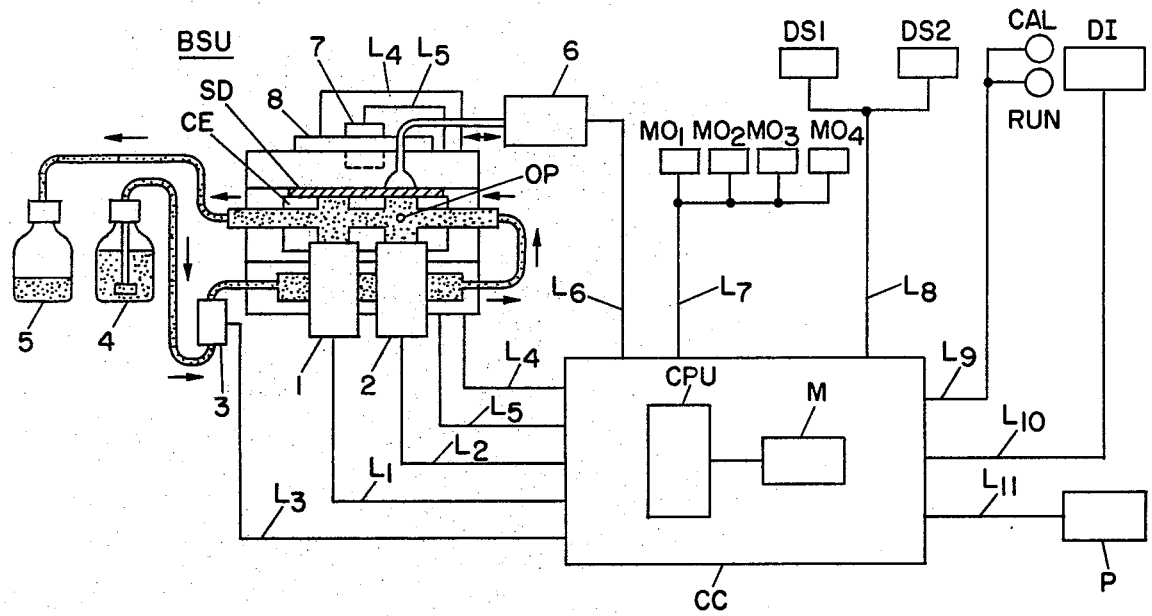
FIG. 1 is a view showing an overall arrangement of a blood sugar analyzer.

While this invention is susceptible of embodiment in many different forms, there is shown in the drawings and will herein be described in detail one specific embodiment, with the understanding that the present disclosure is to be considered as an exemplification of the principles of the invention and is not intended to limit the invention to the embodiment illustrated.

FIG. 1 is a view showing an arrangement of a blood sugar analyzer for analyzing the concentration of blood sugar in a blood specimen.

In FIG. 1, a blood sugar measurement electrode or sensor 1 generates a reaction current proportional to a blood sugar concentration, and comprises an electrode of platinum and silver having on its surface a membrane of blood sugar oxidase attached thereto. The blood sugar measurement electrode 1 and a temperature electrode 2 are disposed in a reaction cell CE. A buffer liquid 4 is delivered by a liquid pump 3 into the cell CE wherein the liquid 4 washes the interior of the cell CE. After a reaction has finished, the buffer liquid 4 is discharged as a drainage liquid 5. An air pump 6 vibrates a silicon diaphragm SD to stir a blood specimen or the like which has been introduced through a inlet port OP into the cell CE, thereby uniformizing the concentration of the blood specimen in the cell CE. A temperature sensor 7 detects the temperature of the cell block. A heater 8 heats the cell block up to temperature of a human body (for example, 37° C.). Thus, the blood in the cell CE is maintained at a temperature equal to a temperature of a human body.

A control device CC composed mainly of a microcomputer CPU is connected to a blood sugar analyzing unit BSU through line $L_1$ through $L_6$. The control device CC reads out a reaction current from the measurement electrode 1 over the line $L_1$, reads out an amount of temperature compensation with respect to a measured value over the line $L_2$, measures and controls the temperature of the cell block over the respective lines $L_4$ and $L_5$, and controls operation of the liquid pump 3 and the air pump 6 over the lines $L_3$ and $L_6$, respectively. The control device CC is also connected to various switches $MO_1$ through $MO_4$, $DS_1$, $DS_2$, a display unit DI, and a printer P through lines $L_7$ through $L_{11}$ for controlling input and output devices and the overall operation of the analyzer. Designated at $DS_1$ is a specimen number setting switch, at $DS_2$ a standard solution value setting switch, at CAL and RUN mode displays for indicating calibration and operation modes, respectively, and at $MO_1$ through $MO_4$ mode setting switches for setting the foregoing modes and a paper feed mode for the printer P, and for setting the switch $DS_1$.

Figure 2:
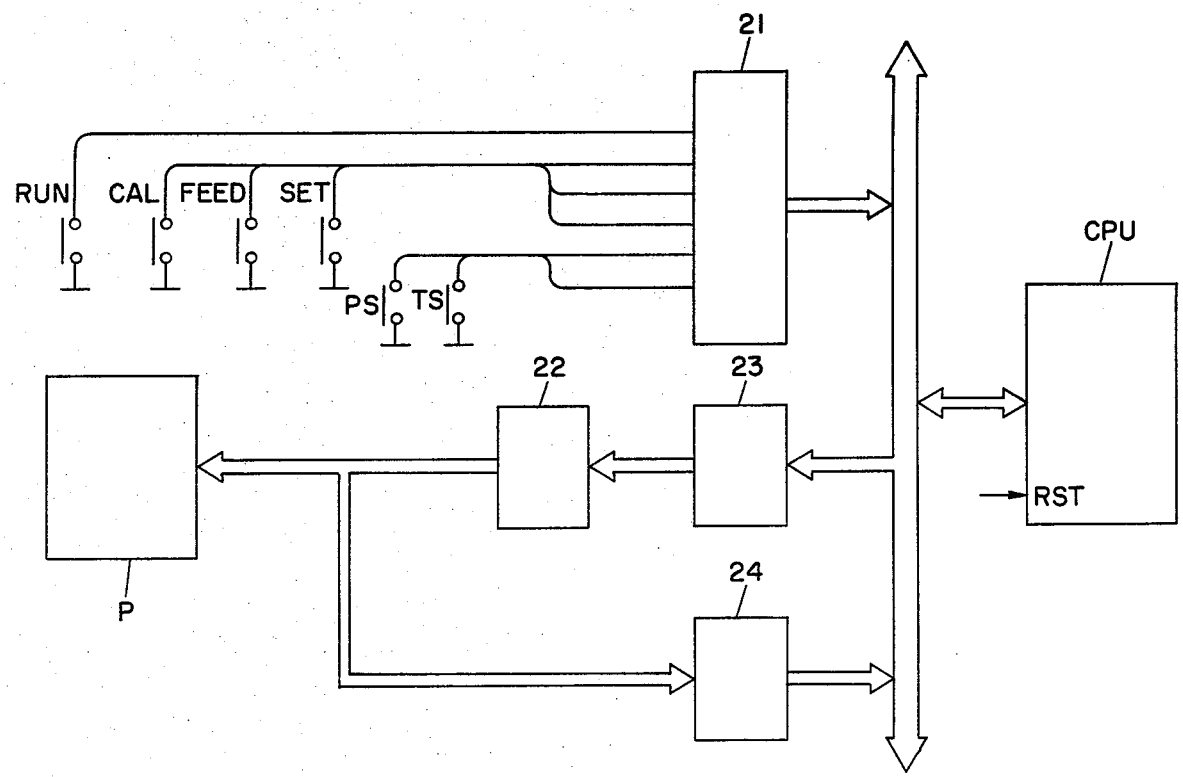
FIG. 2 is a block diagram of an embodiment according to the present invention.
Figure 3:
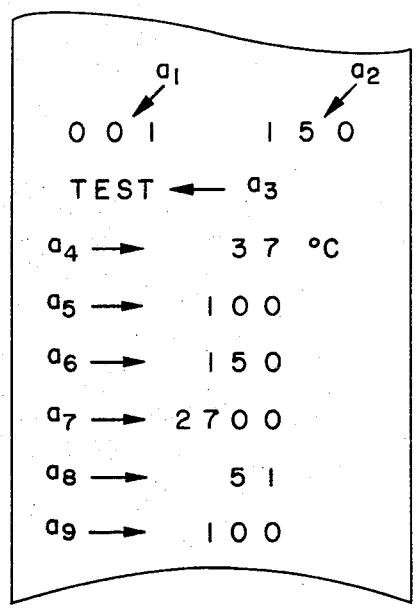
FIG. 3 is a view illustrative of characters printed which indicate types of maintenance information.

FIG. 2 is a block diagram of an embodiment of the invention, and FIG. 3 is a view illustrative of characters printed by a printer in accordance with the present invention.

A printer P is connected to a microcomputer CPU through a driver 22 and a latch 23 and through a buffer 24. The latch 23 serves to store data delivered from the microcomputer CPU. The driver 22 serves to drive a head, a motor and other parts of the printer P. The buffer 24 serves to buffer control signals from the printer P. A push-button switch PS for maintenance of the analyzer and a push-button switch TS for testing the printer P are connected via a buffer 21 to the microcomputer CPU for supplying commands to print information necessary for the analyzer maintenance and information on testing of the printer P. These switches PS, TS are different from ordinary push-button switches (such as for RUN, CAL and others which will be depressed for operation and calibration), in that the switches PS, TS are installed inside the analyzer apparatus for being acessible to and actuated by maintenance personnel, and not ordinarily by analyzer operators.

When the push-button switch PS is actuated, the microcomputer CPU detects such actuation and delivers an operation command to the printer P through the latch 23 and the driver 22, thereby energizing the motor of the printer P. As the motor starts to operate, the printer P generates a synchronous signal which is supplied to a restart command terminal RST of the microcomputer CPU. As a result, the microcomputer CPU starts executing a printer program for controlling operation of the printer P, whereupon the printer P effects printing operation under the printer program. In the illustrated embodiment, various data or information necessary for the maintenance of a sensor section is printed, including the value of temperature in the vicinity of a blood sugar measuring electrode or sensor, the value of output voltage from the sensor, a value indicating sensitivity of the sensor, a value indicating sensor output per unit time during measurement of a blood sugar concentration, and a value indicating offset voltage, as shown in FIG. 3. FIG. 3 illustrates a specimen number a1, a blood sugar concentration a2, predetermined characters a3 printed when the testing push-button switch TS is depressed, a temperature value a4 in the vicinity of the sensor, conversion coefficients a5 and a6 for converting sensor outputs into corresponding blood sugar concentrations, a measured value a7, an offset value a8, and a sensor output per unit time a9. A unit of temperature "°C." and a unit of sensor output "mV" are printed as desired. Upon reviewing this printed data, the maintenance personnel can easily determine the condition of parts of the analyzer, (particularly the sensor output), and decide whether to take suitable measures such as replacement of a part (such as a blood sugar sensor), or adjustment of parts.

When the push-button switch TS is depressed, for testing the printer P, data is printed in a manner described above, except that a predetermined character pattern, "TEST", may be printed as indicated at a3 in FIG. 3. If such a pattern is printed, the printer and a control unit therefore is deemed normal. On the other hand, if no such characters are printed, the printer or its control unit is regarded as malfunctioning and hence should be inspected and repaired as by replacing parts.

With the foregoing arrangement, the printing function of the printer is utilized to make maintenance information available, allowing maintenance to be effected in a short period of time. The printer and its control unit can be checked for normal operation by causing the printer to print predetermined characters, and hence maintenance thereof can easily be carried out.

A printer control system in accordance with the present invention will now be described.

Figure 4:
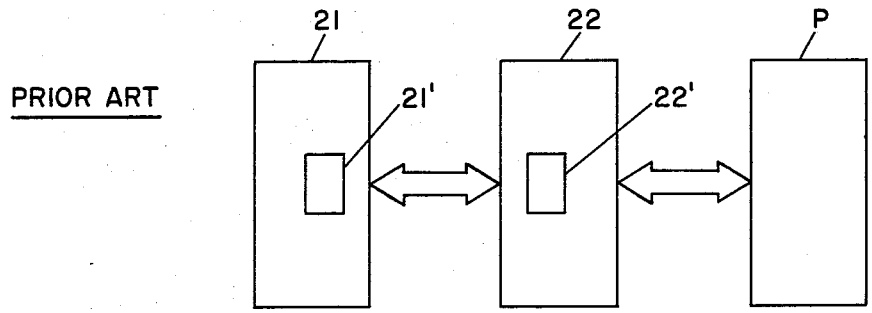
FIG. 4 is a block diagram of a conventional printing control system.

A conventional control system will first be described with reference to FIG. 4. An interface device 22 is interposed between a digital control device 21' and a printer P, and contains a digital control device 22' such as a microcomputer. The interface device 22 in this conventional design is expensive. With the illustrated arrangement, the digital devices are independently incorporated in both a blood sugar analyzer 21 and the interface device 22, and the overall system arrangement is relatively inefficient.

Figure 5:
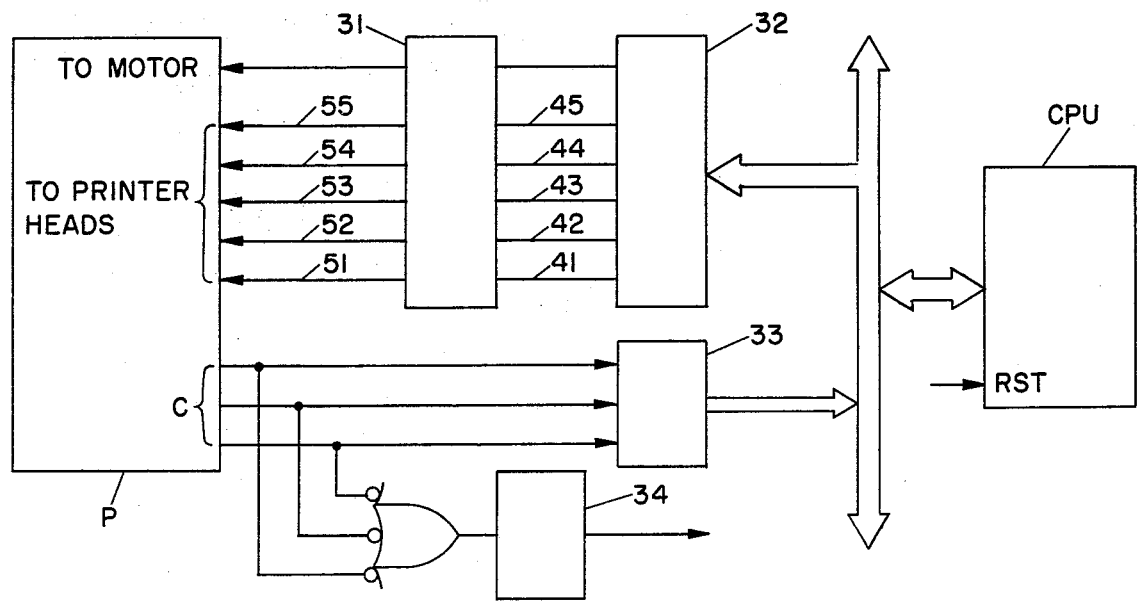
FIG. 5 is a block diagram of a system according to an embodiment of the present invention.
Figure 6:
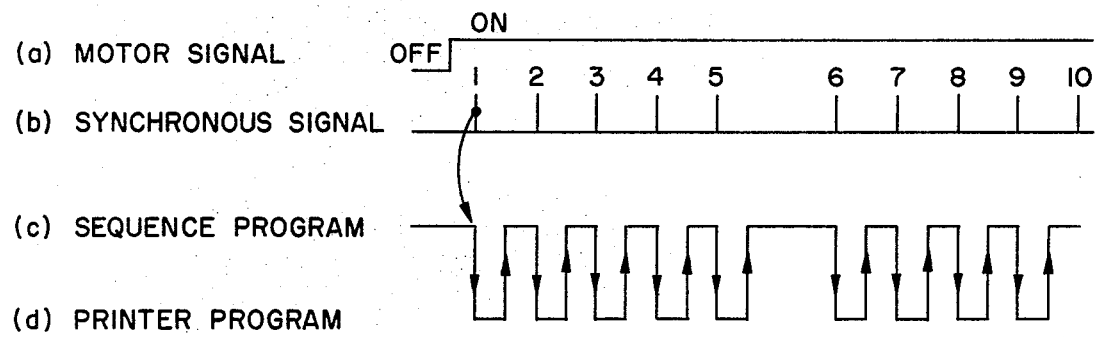
FIG. 6 is a timing diagram showing the waveforms of signals generated in the system illustrated in FIG. 5.
Figure 7:
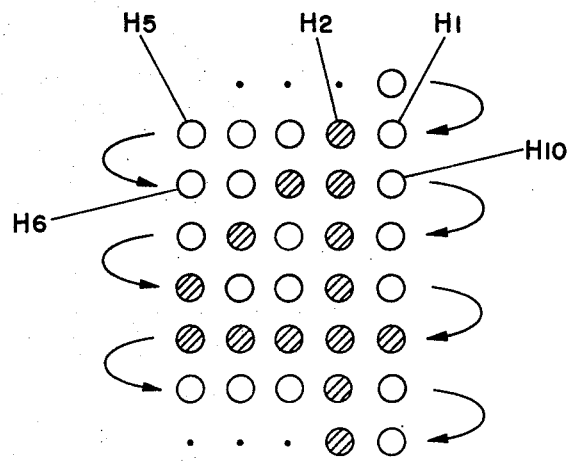
FIG. 7 is a view showing printer heads as they are scanned to define a character to be printed.

FIG. 5 is a block diagram of a system according to an embodiment of the present invention; FIG. 6 is a timing diagram showing the waveforms of signals in the system shown in FIG. 5; and FIG. 7 is a view of printer heads, illustrative of the way in which the heads are scanned to print a character.

An interface system according to the present invention comprises a latch 32 for temporarily storing data from a microcomputer CPU which serves as a control device for the analyzer, a driver 31 for energizing printer heads, a printer motor and other parts (not shown) of a printer P, buffers 33, 34 for receiving control signals C such as a synchronous signal generated by the printer P, and for supplying them to the microcomputer CPU.

When a start signal is supplied from the microcomputer CPU to the printer P via the latch 32 and the driver 31, the motor of the printer P is first energized as shown at (a) in FIG. 6. As the motor starts operating to feed paper in the printer P, the printer generates a synchronous signal which is delivered as a restart signal or an interruption signal to the RST terminal of the microcomputer CPU. At this time, the microcomputer CPU interrupts execution of a sequence program as indicated at (c) in FIG. 6 and starts execution of a printer program as indicated at (d) in FIG. 6. Such a switching operation is carried out each time the microcomputer CPU is supplied with a synchronous signal from the printer P. The repetitive switching causes printer heads (FIG. 7) to be subjected to helical scanning for defining a predetermined character pattern. At this time, the printer program controls the microcomputer to energize desired printer heads by selectively energizing and de-energizing driver units with signals corresponding to a given character dot pattern stored in a memory in the microcomputer CPU. In accordance with the printer program, the CPU generates an output control signal sequence to gate the outputs on leads 41 to 45 (FIG. 5) and 51 to 55, so that the first synchronous signal provides output data on lead 41 (and 51) corresponding to dot #1, (H1), the second synchronous signal provides output data on lead 42 (and 52) corresponding to dot #2, (H2). Similarly, heads H3 through H10 and so on are successively selected for helical scanning of the printer heads to define a character pattern "4" with heads which are energized according to the content of the memory at the time.

When printing is finished, the motor is deenergized to stop operation of the printer P.

With the above arrangement of the present invention, an interface function is incorporated in a control device, and hence the interface device used may be of a simple construction composed mainly of a driver and buffers. A costly interface device which has been conventionally required is not necessary. Further communication with a printer is rendered possible inexpensively on a real-time basis.

While in the foregoing embodiment an interface control system for a printer for use with a blood sugar analyzer is described, the present invention is also applicable to control systems for interfaces between general digital control devices and printers.

From the foregoing, it will be observed that numerous variations and modifications may be effected without departing from the true spirit and scope of the novel concept of the invention. It is to be understood that no limitation with respect to the specific embodiments illustrated herein is intended or should be inferred. It is, of course, intended to cover by the appended claims all such modifications as fall within the scope of the claims.

What is claimed is:

1. A blood sugar analyzer having a reaction cell which houses a fixed enzyme membrane and a measuring electrode and which receives a blood specimen, to cause a chemical reaction between the blood specimen and the fixed enzyme membrane, for measuring the blood sugar concentration in the blood specimen on the basis of a reaction current generated in the measuring electrode by the chemical reaction, and including means for monitoring the temperature in the reaction cell, means for displaying informational data on the temperature to an operator in response to said monitoring means, and manually actuable input means for providing a test display signal, and wherein said display means displays a predetermined character pattern in response to said test display signal.

2. The blood sugar analyzer according to claim 1, wherein the means for displaying comprises a printer, and including a digital control device for executing automatic control operation of the analyzer in response to a predetermined sequence program and for enabling the printer to print measurement results in response to a printer controlling program, said digital control device being transferred from a sequence program operational mode to a printer controlling program operational mode in response to interrupt signals supplied at periodic time intervals as restart signals from the printer.

3. The blood sugar analyzer according to claim 1, wherein the monitoring means includes means for monitoring the sensitivity of the measuring electrode, and wherein the display means includes means for displaying informational data on the sensitivity to an operator in response to said monitoring means.

4. the blood sugar analyzer according to claim 1, wherein the display means comprises a printer.

* * * * *